(12) United States Patent
Miyamoto

(10) Patent No.: US 9,016,273 B2
(45) Date of Patent: Apr. 28, 2015

(54) INHALER AID WITH REED FOR MINUTE POWDERY CURATIVE MEDICINE

(76) Inventor: Akihiko Miyamoto, Sakuragawa (JP)

( * ) Notice: Subject to any disclaimer, the term of this patent is extended or adjusted under 35 U.S.C. 154(b) by 1807 days.

(21) Appl. No.: 10/578,624

(22) PCT Filed: Feb. 19, 2004

(86) PCT No.: PCT/JP2004/001902
§ 371 (c)(1),
(2), (4) Date: Apr. 12, 2007

(87) PCT Pub. No.: WO2005/079896
PCT Pub. Date: Sep. 1, 2005

(65) Prior Publication Data
US 2007/0272235 A1    Nov. 29, 2007

(51) Int. Cl.
*A61M 15/00* (2006.01)
(52) U.S. Cl.
CPC ......... *A61M 15/00* (2013.01); *A61M 2202/064* (2013.01); *A61M 2205/43* (2013.01); *A61M 15/0021* (2014.02)
(58) Field of Classification Search
CPC .............. A61C 5/14; B63C 11/16; A62B 9/06
USPC ............. 128/200.14, 200.19, 200.22–200.24, 128/200.26, 203.12–203.15, 203.19, 128/203.21, 203.23–203.25, 859–862
See application file for complete search history.

(56) References Cited

U.S. PATENT DOCUMENTS

| | | | | |
|---|---|---|---|---|
| 4,291,688 A | * | 9/1981 | Kistler | 128/200.23 |
| 4,809,692 A | | 3/1989 | Nowacki et al. | |
| 5,042,467 A | * | 8/1991 | Foley | 128/200.23 |
| 5,062,422 A | | 11/1991 | Kinkade | |
| 5,477,849 A | * | 12/1995 | Fry | 128/200.14 |
| 5,492,112 A | * | 2/1996 | Mecikalski et al. | 128/203.15 |
| 5,669,378 A | * | 9/1997 | Pera et al. | 128/203.21 |
| 5,848,588 A | * | 12/1998 | Foley et al. | 128/200.23 |

(Continued)

FOREIGN PATENT DOCUMENTS

| | | |
|---|---|---|
| JP | 2-104052 | 8/1990 |
| JP | 2-215475 A | 8/1990 |

(Continued)

OTHER PUBLICATIONS

International Search Report mailed Jul. 6, 2004 of International Application PCT/JP2004/001902.

*Primary Examiner* — Rachel Young
(74) *Attorney, Agent, or Firm* — Westerman, Hattori, Daniels & Adrian, LLP

(57) ABSTRACT

The present invention provides an inhaler aid which maximizes utility of an inhaler for the minute powdery curative medicine, and which is used by being attached to the inhaler so that people including a user can objectively ascertain in each case whether an inhalation operation has been correctly performed. In the present invention, the inhaler aid with the reed for the minute powdery curative medicine has a configuration characterized in that the reed is fitted into a right side of a main unit made of silicon rubber, and the inhaler aid is attached to a mouthpiece portion of a conventionally used inhaler for the minute powdery curative medicine such that the aid equipped with the reed is placed between the inhaler for the minute powdery curative medicine and a mouth of a patient, and when an intake operation has been correctly performed, a sound is produced.

3 Claims, 15 Drawing Sheets

(56) References Cited

U.S. PATENT DOCUMENTS

| | | | |
|---|---|---|---|
| 6,026,807 A | * | 2/2000 | Puderbaugh et al. .... 128/200.23 |
| 6,578,571 B1 | | 6/2003 | Watt |
| 2002/0040713 A1 | * | 4/2002 | Eisele et al. ............ 128/203.21 |
| 2002/0046751 A1 | * | 4/2002 | MacRae et al. .......... 128/200.22 |
| 2002/0104531 A1 | * | 8/2002 | Malone .................... 128/200.23 |
| 2002/0121275 A1 | * | 9/2002 | Johnson et al. ......... 128/200.22 |
| 2004/0182387 A1 | * | 9/2004 | Steiner et al. ............ 128/203.15 |
| 2004/0244794 A1 | * | 12/2004 | Richards .................. 128/203.15 |

FOREIGN PATENT DOCUMENTS

| | | |
|---|---|---|
| JP | 2-271871 A | 11/1990 |
| WO | WO99/53982 A1 | 10/1999 |

* cited by examiner

INHALER AID WITH REED FOR MINUTE POWDERY CURATIVE MEDICINE

TECHNICAL FIELD

The present invention relates to an inhaler aid with a reed for a minute powdery curative medicine, which is used as an aid when a patient with bronchial asthma or a chronic obstructive lung disease uses an inhaler to inhale a minute powdery curative medicine, and which makes a sound so that the patient himself can ascertain that an inhalation operation has been achieved without fail.

BACKGROUND ART

Heretofore, curative medicines for bronchial asthma or a chronic obstructive lung disease were mainly internal medicines, but later, a type of inhaler for atomization and inhalation of liquid medicines using a small cylinder charged with chlorofluorocarbon has been developed.

As is well known, chlorofluorocarbon is a cause of environmental destruction and its effects on the human body are concerned. Therefore, such a type of curative medicines have recently been prevailed that a patient himself inhales the minute powdery medicine with intake force, and hence inhalers for the minute powdery curative medicine with various configurations and shapes are used.

Common points of the inhalers for the minute powdery curative medicine are that intake air of the patient himself whirls up the minute powdery medicine in a medicine chamber, causes a vortex flow, and lets the medicine through a grating to equally diffuse minute powder so that it is inhaled from a mouthpiece into an oral cavity, and further into a respiratory tract of the patient. They are also common in that an air intake hole is provided for correcting a lung breathing capacity and an air flow volume in a minute powdery medicine inhalation path to prevent breathing difficulty.

However, the conventional type of inhalers for self inhalation of the minute powdery curative medicine have a disadvantage that the patient himself can not ascertain whether or not the inhalation has been achieved without fail because the amount of minute particle curative medicine is significantly small.

Furthermore, patients, especially elderly people and children, are not able to perform an inhalation operation itself, and might blow the mouthpiece, so that the patients can not actually use the curative medicine properly.

Therefore, an object of the present invention is to provide an inhaler aid which maximizes utility of the inhaler for the minute powdery curative medicine, and which is used by being attached to the inhaler so that people including a user can objectively ascertain in each case whether the inhalation operation has been correctly performed.

DISCLOSURE OF THE INVENTION

In order to solve the problems described above, an inhaler aid with a reed for a minute powdery curative medicine of the present invention is characterized in that the reed is fitted into a right side of a main unit made of silicon rubber, and the inhaler aid is attached to a mouthpiece portion of a conventionally used inhaler for the minute powdery curative medicine such that the aid equipped with the reed is placed between the inhaler for the minute powdery curative medicine and a mouth of a patient, and when an intake operation has been performed without fail, a sound is produced.

BEST MODE FOR CARRYING OUT THE INVENTION

Figure 5:
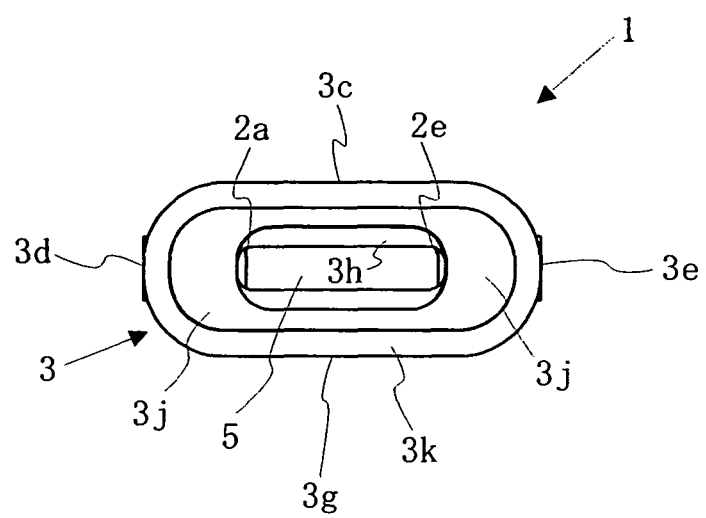
FIG. 5 is a bottom plan view of the inhaler aid with the reed for the minute powdery curative medicine of the present invention.
Figure 6:
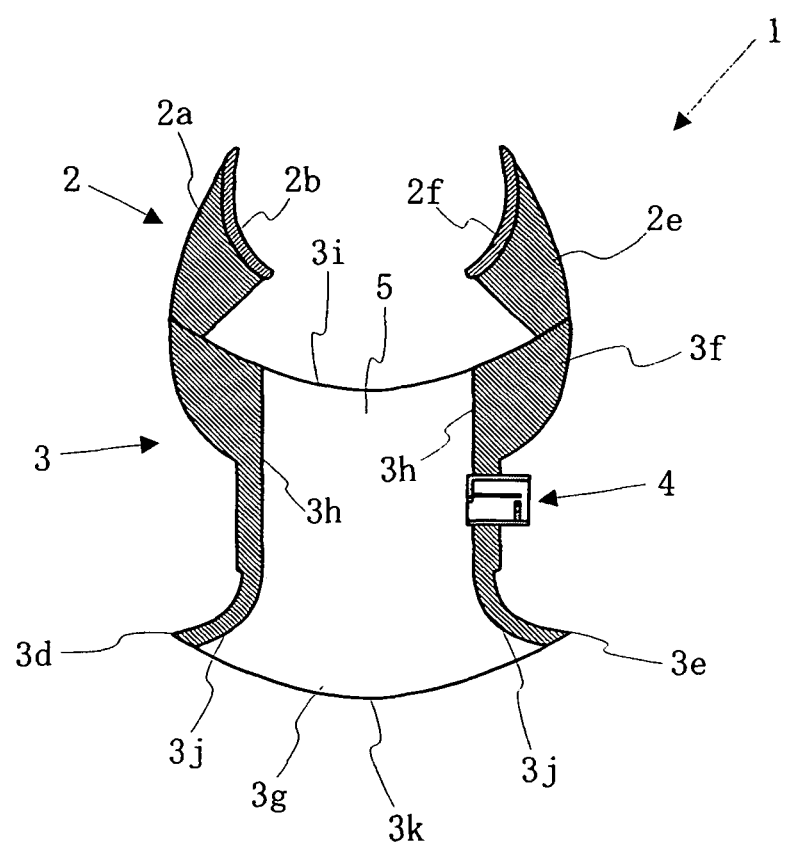
FIG. 6 is a sectional view of the inhaler aid with the reed for the minute powdery curative medicine of the present invention.
Figure 7:
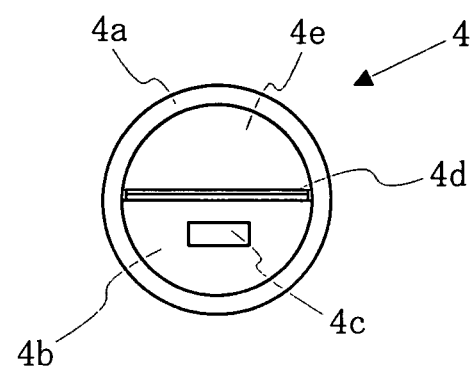
FIG. 7 is a right side view of the reed used in the inhaler aid with the reed for the minute powdery curative medicine of the present invention.
Figure 8:
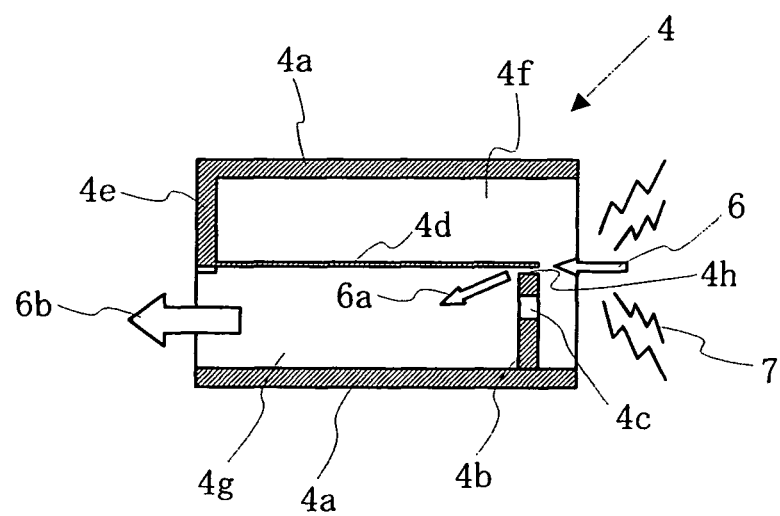
FIG. 8 is a sectional view of the reed used in the inhaler aid with the reed for the minute powdery curative medicine of the present invention.
Figure 9:
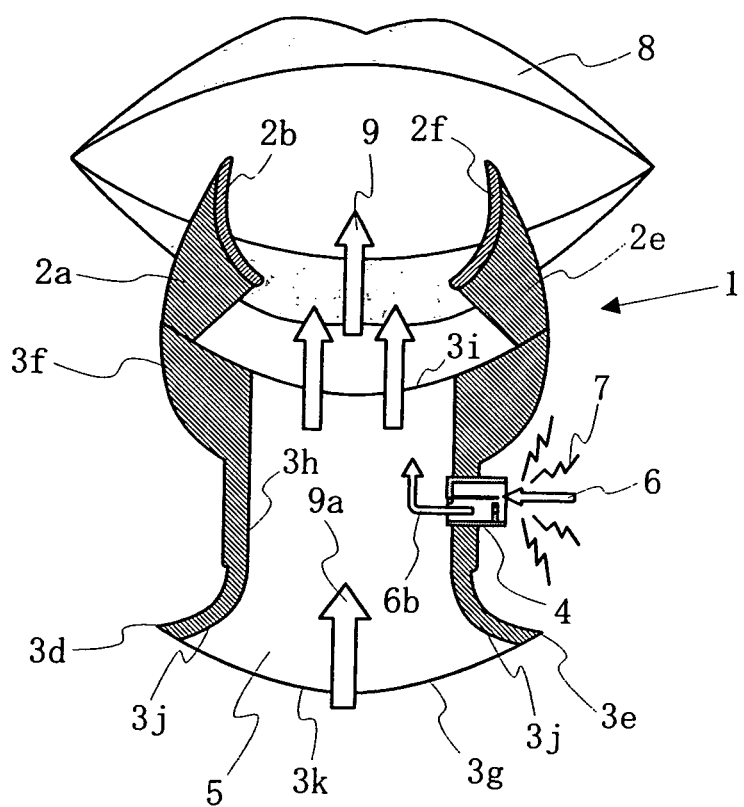
FIG. 9 is a sectional view showing a mechanism of the inhaler aid with the reed for the minute powdery curative medicine of the present invention.

An inhaler aid with a reed for a minute powdery curative medicine of the present invention will hereinafter be described in detail in reference to the accompanying drawings. FIG. 1 to FIG. 6 are views showing the inhaler aid with the reed for the minute powdery curative medicine of the present invention, FIG. 7 and FIG. 8 are views showing the reed used in the inhaler aid with the reed for the minute powdery curative medicine of the present invention, FIG. 9 is a view showing a mechanism of the inhaler aid with the reed for the minute powdery curative medicine of the present invention, and FIG. 10 to FIG. 15 are views showing used states of the inhaler aid with the reed for the minute powdery curative medicine of the present invention which is attached to conventional inhalers for the minute powdery curative medicine.

Figure 1:
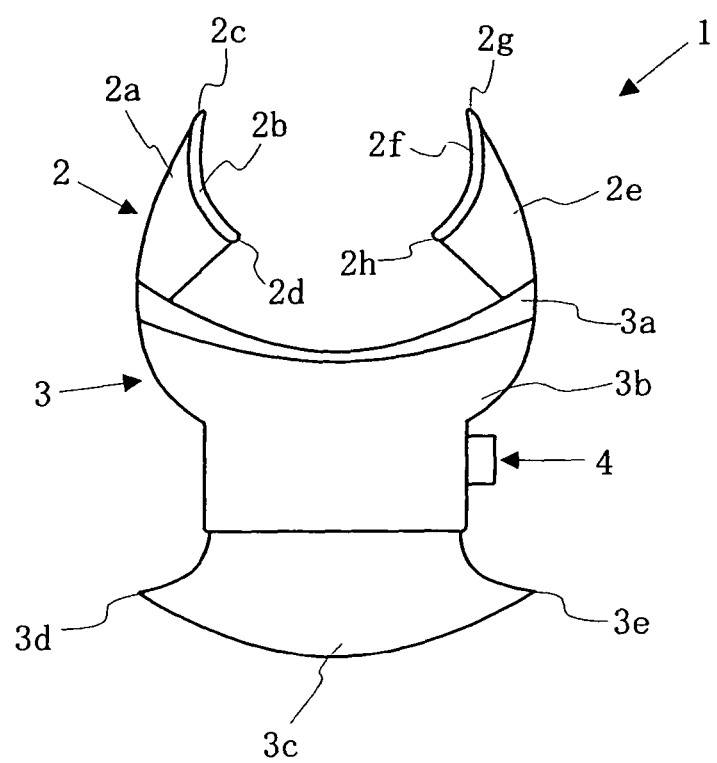
FIG. 1 is a front view of an inhaler aid with a reed for a minute powdery curative medicine of the present invention; is a right side view of the inhaler aid with the reed for the minute powdery curative medicine of the present invention.
Figure 2:
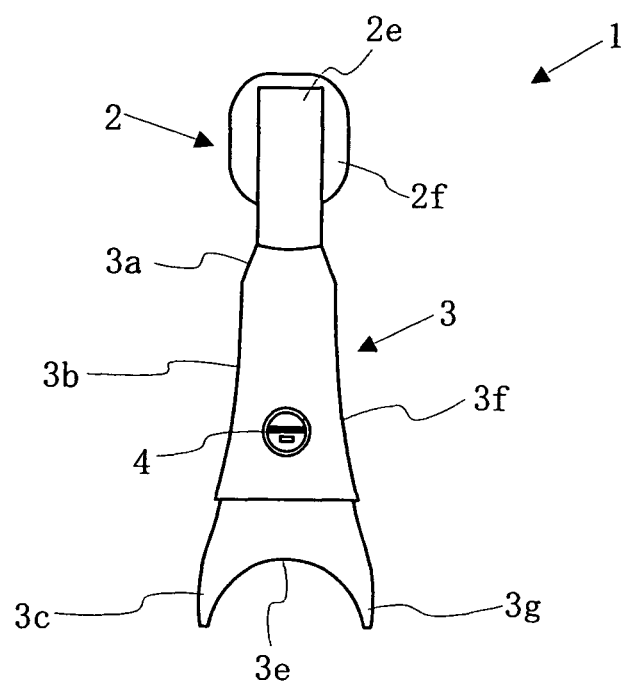
Figure 3:
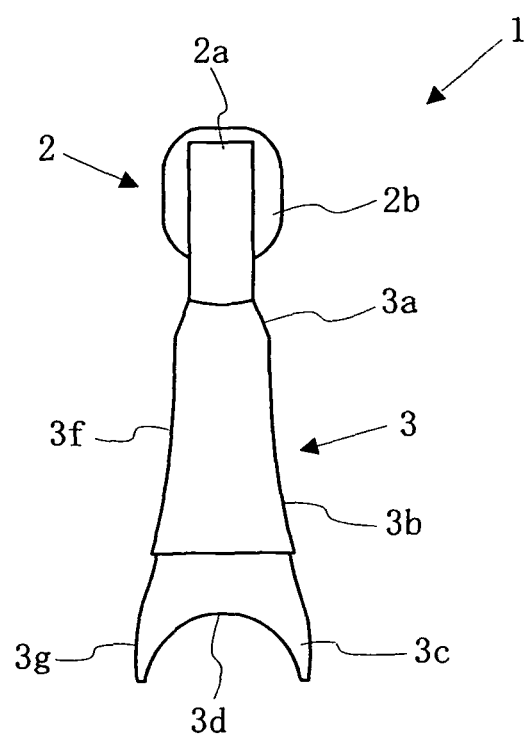
FIG. 3 is a left side view of the inhaler aid with the reed for the minute powdery curative medicine of the present invention.
Figure 4:
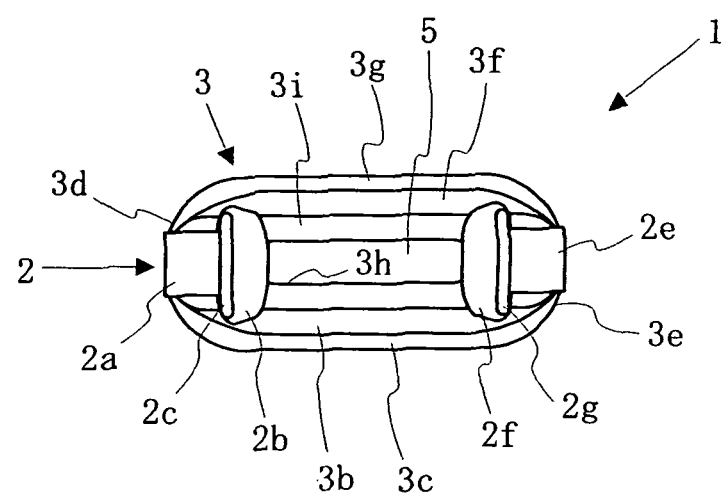
FIG. 4 is a plan view of the inhaler aid with the reed for the minute powdery curative medicine of the present invention.

FIG. 1 is a front view of the inhaler aid with the reed for the minute powdery curative medicine of the present invention, FIG. 2 is a right side view of the inhaler aid with the reed for the minute powdery curative medicine of the present invention; FIG. 3 is a left side view of the inhaler aid with the reed for the minute powdery curative medicine of the present invention; FIG. 4 is a plan view of the inhaler aid with the reed for the minute powdery curative medicine of the present invention; FIG. 5 is a bottom plan view of the inhaler aid with the reed for the minute powdery curative medicine of the present invention; FIG. 6 is a sectional view of the inhaler aid for the minute powdery curative medicine of the present invention.

As shown in FIG. 1 to FIG. 3, an inhaler aid 1 with the reed for the minute powdery curative medicine of the present invention is comprised of a main unit 3, an engagement portion 2 provided on the main unit 3, and a reed 4 attached to a right side portion of the main unit 3.

In the main unit 3, an upper edge 3a is formed at an upper portion, which extends in both right and left directions, of a tube 3b, and at a lower portion of the tube 3b, a horn-shaped junction is provided which comprises a front joint piece 3c, a left end 3d, a right end 3e and a rear joint piece 3g. Moreover, a hole for inserting the reed 4 is formed at a right side portion of the tube 3b.

The engagement portion 2 provided on the main unit 3 is constituted of a left projection 2a comprising an elliptical holding member 2b at the end, and a right projection 2e which is symmetrical to the left projection 2a and comprises an elliptical holding member 2f at the end.

The holding member 2b provided in the left projection 2a of the engagement portion 2 has a large thickness, and is gently curved from an upper end 2c toward a lower end 2d. Further, similarly to the holding member 2b, the holding member 2f provided in the right projection 2e is also curved gently from an upper end 2g toward a lower end 2h.

As shown in FIG. 4 to FIG. 5, an outer peripheral surface 3f of the tube 3b forming the main unit 3 is almost elliptical, and an inner peripheral surface 3h is also almost elliptical. An inhalation hole 3i is formed at an upper portion of the tube 3b.

Furthermore, as shown in FIG. 5, a junction inner peripheral portion 3j of the junction, which is provided at the lower portion of the main unit 3 and comprises the front joint piece 3c, the left end 3d, the right end 3e and the rear joint piece 3g, is formed so as to taper from a junction aperture 3k toward the lower portion of the tube 3b.

As shown in FIG. 6, the inner peripheral surface 3h inside the tube 3b and the junction inner peripheral portion 3j inside the junction form an inhalation path 5, and the reed 4 fitted into the right side portion of the tube 3b is inserted to project through the tube 3b and further slightly into the inhalation path 5.

FIG. 7 is a right side view of the reed used in the inhaler aid with the reed for the minute powdery curative medicine of the present invention, and FIG. 8 is a sectional view of the reed used in the inhaler aid with the reed for the minute powdery curative medicine of the present invention.

As shown in FIG. 7 to FIG. 8, the reed 4 is cylindrical, and a semi-circular projecting plate 4b in which a rectangular hole 4c is formed is provided at a right end of a tube 4a, and at a left end, a semi-circular block plate 4e is continuously provided at a left end upper portion of the tube 4a.

A valve 4d having a length up to a position of the projecting plate 4b is continuously provided in the block plate 4e. The valve 4d divides the inside of the tube 4a into a resonance chamber 4f and a flow chamber 4g, and a clearance 4h is formed between the valve 4d and an upper portion of the projecting plate 4b.

When an air 6 is sucked into the reed 4, the valve 4d vibrates when an air 6a passes through the clearance 4h formed between the valve 4d and the projecting plate 4b. The vibration of the valve 4d resonates within the resonance chamber 4f, and produces a beep 7.

The air 6a vibrates the valve 4d when it passes through the clearance 4h to make a sound from the reed 4, and an air 6b passes through the flow chamber 4g to be released to the outside of the reed 4.

FIG. 9 is a sectional view showing a mechanism of the inhaler aid with the reed for the minute powdery curative medicine of the present invention. As shown in FIG. 9, when a patient uses the inhaler aid 1 with the reed for the minute powdery curative medicine, the patient holds the engagement portion 2 in a mouth 8, and bites and fixes the left and right projections 2a and 2e with teeth. At this moment, the holding members 2b and 2f hold teeth.

If the patient breathes in an air 9 while holding and fixing the engagement portion 2 in the mouth 8, an air 9a is sucked in from the junction aperture 3k at a lower portion of the inhaler aid 1 with the reed for the minute powdery curative medicine, and at the same time, the air 6 is sucked in also from the reed 4, so that the reed 4 produces the beep 7.

The air 9a sucked in from the junction aperture 3k is inhaled into an oral cavity through the inhalation path 5, and the air 6b sucked in from the reed 4 and released into the inhalation path 5 is combined with the air 9a sucked in from the junction aperture 3k in the inhalation path 5, and is inhaled into the oral cavity. Therefore, if the inhaler aid 1 with the reed for the minute powdery curative medicine is used, the beep 7 is produced when the air is correctly inhaled, thereby making it possible to recognize that an inhalation operation has been correctly performed.

The inhaler aid 1 with the reed for the minute powdery curative medicine of the present invention is made of silicon rubber. Therefore, it excels in flexibility, toughness, safety and the like, and can easily be cleaned. Moreover, as it is made of silicon rubber, when one masters the use of the inhaler aid 1 with the reed for the minute powdery curative medicine of the present invention and can use it by only holding it in the mouth 8 without biting and fixing the projections 2a and 2e of the engagement portion 2 with teeth, the projections 2a and 2e can easily be cut away.

Furthermore, as the inhaler aid 1 with the reed for the minute powdery curative medicine of the present invention is made of silicon rubber, it excels in flexibility, and can be used by being attached to various kinds of inhalers for the minute powdery curative medicine that have conventionally been used.

FIG. 10 to FIG. 15 show the inhaler aid with the reed for the minute powdery curative medicine of the present invention which is used by being attached to various kinds of inhalers for the minute powdery curative medicine that have conventionally been used.

Figure 10:
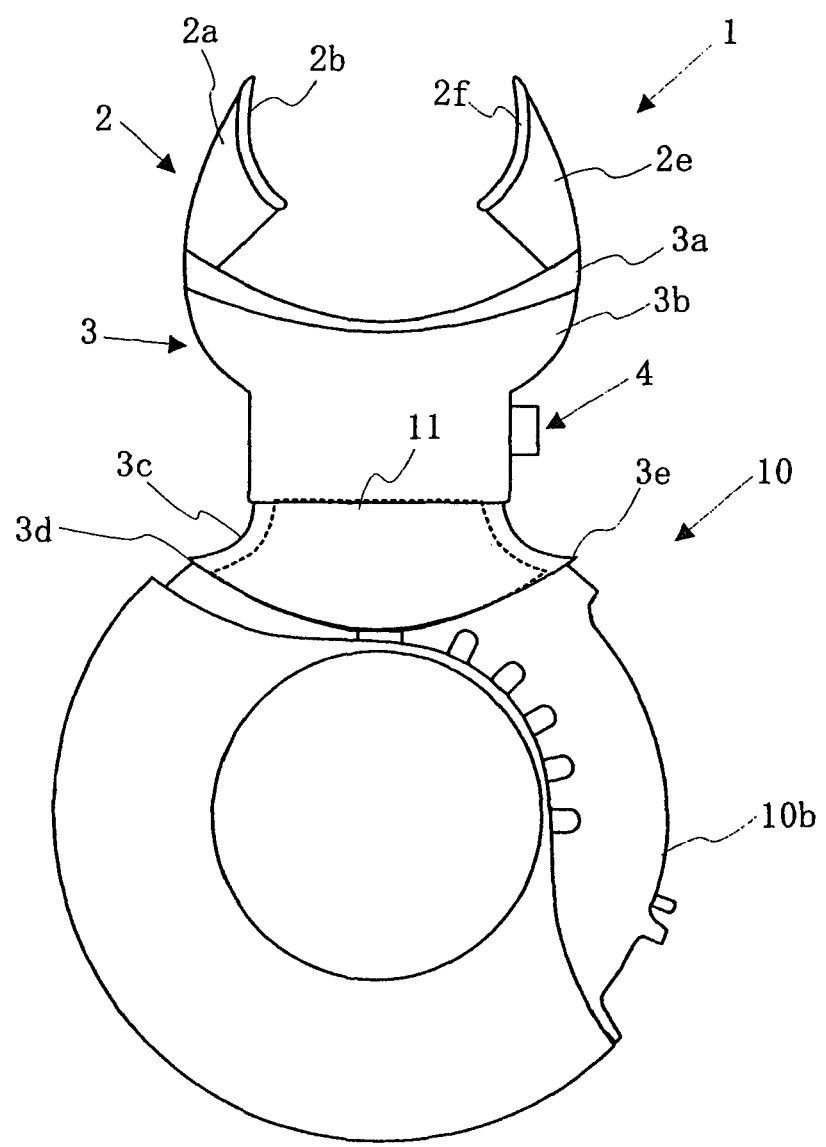
FIG. 10 is a front view when the inhaler aid with the reed for the minute powdery curative medicine of the present invention is used with a FLUTIDE DISCUS (registered trademark)
Figure 11:
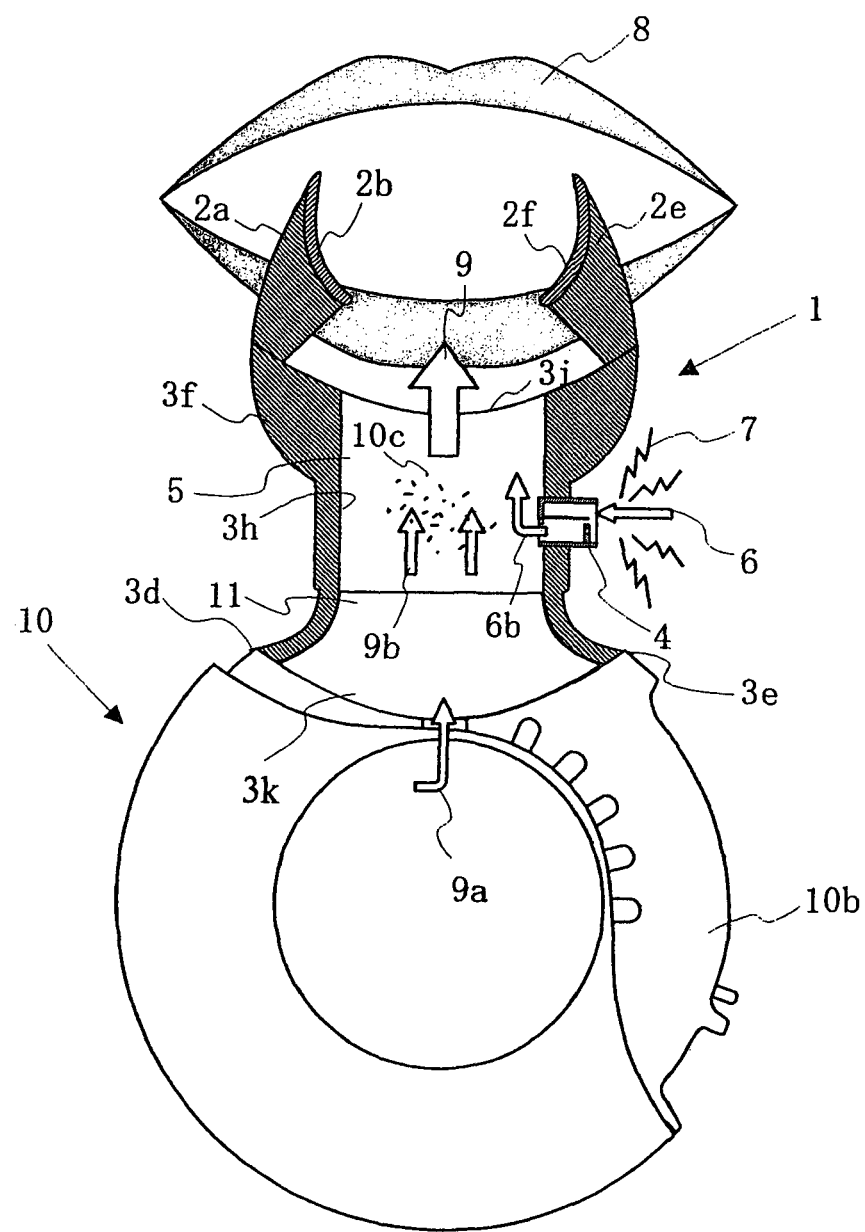
FIG. 11 is a partial sectional view when the inhaler aid with the reed for the minute powdery curative medicine of the present invention is used with a FLUTIDE DISCUS (registered trademark)

FIG. 10 and FIG. 11 are views showing the inhaler aid with the reed for the minute powdery curative medicine of the present invention which is used by being attached to a FLUTIDE DISCUS (registered trademark), a conventionally used inhaler for the minute powdery curative medicine manufactured by GlaxoSmithKline Corporation.

As shown in FIG. 10, in order to use the inhaler aid 1 with the reed for the minute powdery curative medicine of the present invention by attaching it to a FLUTIDE DISCUS (registered trademark) 10 which is the conventionally used inhaler for the minute powdery curative medicine, the following attachment method is implemented wherein a mouthpiece 11 of the FLUTIDE DISCUS (registered trademark) 10 is inserted into and joined to the junction aperture 3k of the junction, which comprises the front joint piece 3c, the left end 3d, the right end 3e and the rear joint piece 3g, of the inhaler aid 1 with the reed for the minute powdery curative medicine.

The junction of the inhaler aid 1 with the reed for the minute powdery curative medicine has a horn shape, so that when it is joined to the mouthpiece 11, both sides of the mouthpiece 11 fit close to the curved shape, thereby enabling close contact attachment.

As shown in FIG. 11, the FLUTIDE DISCUS (registered trademark) 10 to which the inhaler aid 1 with the reed for the minute powdery curative medicine is attached is used in the following method; the patient first holds the engagement portion 2 in the mouth 8, and bites and fixes the projections 2a and 2e of the engagement portion 2 with teeth, and then breathes in the air 9.

At this moment, the inhaler aid 1 with the reed for the minute powdery curative medicine is attached only for the purpose of aiding a portion of the mouthpiece 11 without interfering with the mechanism inherent to the FLUTIDE DISCUS (registered trademark) 10, so that it is attached without blocking an air hole and the like necessary to inhale the curative medicine.

Therefore, if the patient holds the engagement portion 2 in the mouth 8 and breathes in the air 9, the air 9a is sucked from the air hole of the FLUTIDE DISCUS (registered trademark) 10. The air 9a whirls up a curative medicine 10c from a medicine chamber mounted in a main unit 10b and is released together with the curative medicine 10c from the mouthpiece 11 into the inhalation path 5 of the inhaler aid 1 with the reed for the minute powdery curative medicine, and then inhaled into the oral cavity through the inhalation path 5.

At the same time, the patient breathes in the air 9 to cause the air 6 also to be sucked into the reed 4 inserted in the right side of the inhaler aid 1 with the reed for the minute powdery curative medicine, and thus the valve 4d is vibrated, and the air 6b is released into the inhalation path 5 of the inhaler aid 1 with the reed for the minute powdery curative medicine, whereby the reed 4 produces the beep 7. This allows the patient to know that the curative medicine 10c has been correctly inhaled.

Figure 12:
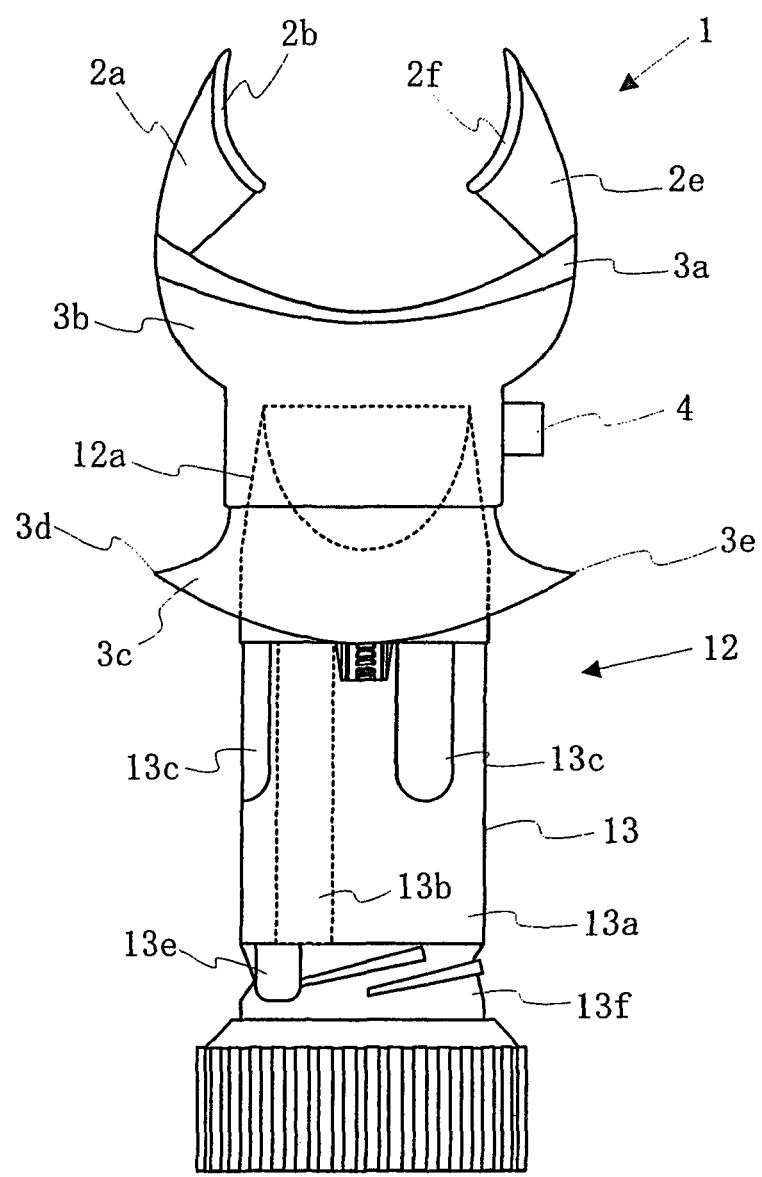
FIG. 12 is a front view when the inhaler aid with the reed for the minute powdery curative medicine of the present invention is used with a PULMICORT TURBUHALER (registered trademark)
Figure 13:
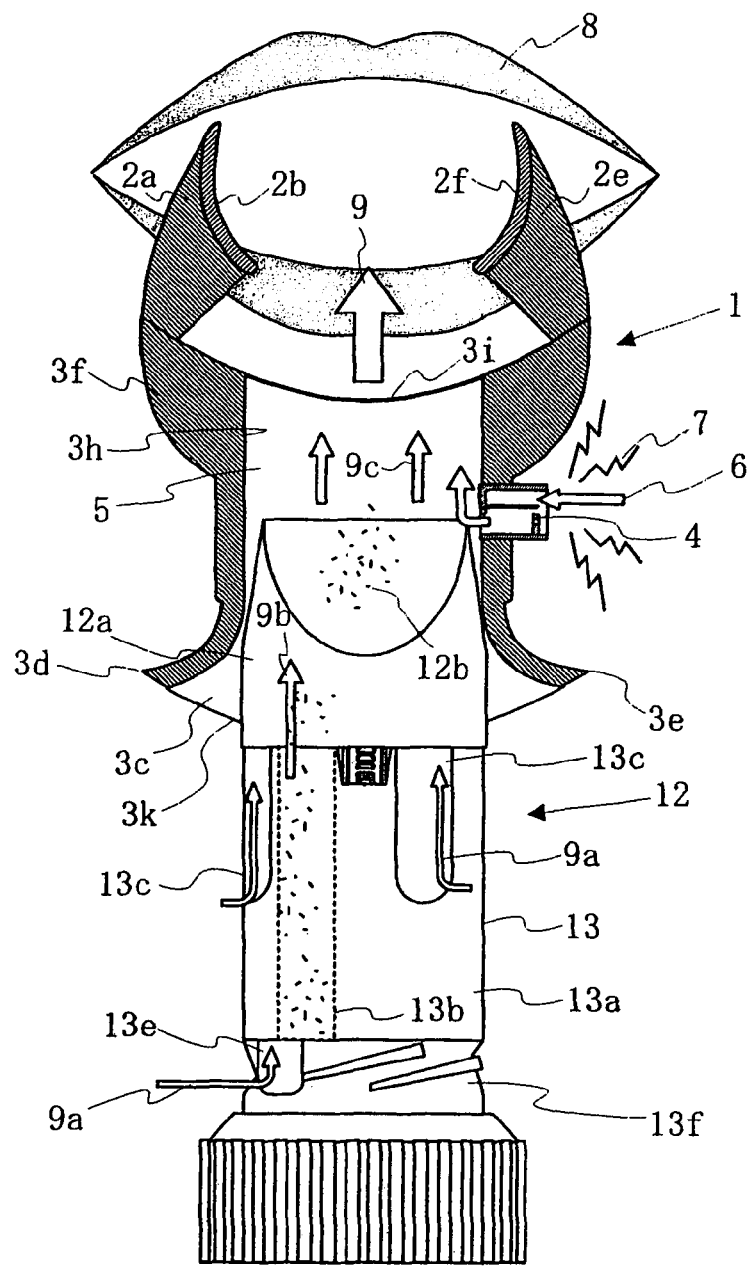
FIG. 13 is a partial sectional view when the inhaler aid with the reed for the minute powdery curative medicine of the present invention is used with the PULMICORT TURBUHALER (registered trademark)

FIG. 12 and FIG. 13 are views showing the inhaler aid with the reed for the minute powdery curative medicine of the present invention which is used by being attached to a PULMICORT TURBUHALER (registered trademark), a conventionally used inhaler for the minute powdery curative medicine manufactured by AstraZeneca Corporation.

The inhaler aid 1 with the reed for the minute powdery curative medicine of the present invention is attached to a PULMICORT TURBUHALER (registered trademark) 12 which is the conventionally used inhaler for the minute powdery curative medicine, in the following attachment method. As shown in FIG. 12, a mouthpiece 12a provided at an upper portion of the PULMICORT TURBUHALER (registered trademark) 12 is inserted into and joined to the junction aperture 3k of the inhaler aid 1 with the reed for the minute powdery curative medicine.

As shown in FIG. 12, air intake grooves 13c for taking in the air for the PULMICORT TURBUHALER (registered trademark) 12 are provided in a longitudinally long shape on an upper outer peripheral surface of a tube 13a of a main unit 13, and an air hole 13e is further provided in a fitting portion 13f attached to a lower portion of the tube 13a. Therefore, even when the inhaler aid 1 with the reed for the minute powdery curative medicine is attached to the mouthpiece 12a, the inhaler aid 1 with the reed for the minute powdery curative medicine does not block the mechanism for air intake or the like that the PULMICORT TURBUHALER (registered trademark) 12 has.

As shown in FIG. 13, since the inhaler aid 1 with the reed for the minute powdery curative medicine of the present invention is made of flexible silicon rubber, the inner peripheral surface 3h of the inhaler aid 1 with the reed for the minute powdery curative medicine closely contacts and is firmly attached to a lower cylindrical portion of the mouthpiece 12a even when an upper tapered portion of the mouthpiece 12a is inserted into the inhalation path 5.

The PULMICORT TURBUHALER (registered trademark) to which the inhaler aid 1 with the reed for the minute powdery curative medicine is attached is used in the following manner. First, the patient holds the engagement portion 2 in the mouth 8, and bites and fixes the projections 2a and 2e with teeth, and then breathes in the air 9.

Then, in the PULMICORT TURBUHALER (registered trademark) 12, the airs 9a, 9a are taken into the main unit 13 from the air intake grooves 13c and the air hole 13e that are formed in the main unit 13, and an air 9b taken in from the air hole 13e whirls up a curative medicine 12b in an inhalation medicine tube 13b, and then the curative medicine 12b is released together with an air 9c from the mouthpiece 12a into the inhalation path 5, whereby the curative medicine 12b is inhaled together with the air into the oral cavity.

At the same time, the air 6 is sucked also into the reed 4 inserted in the right side of the inhaler aid 1 with the reed for the minute powdery curative medicine, and the air which has vibrated the valve 4d is released from the reed 4 into the inhalation path 5, thereby producing the beep 7. This allows the patient to know that the curative medicine 12b has been correctly inhaled into the oral cavity.

Figure 14:
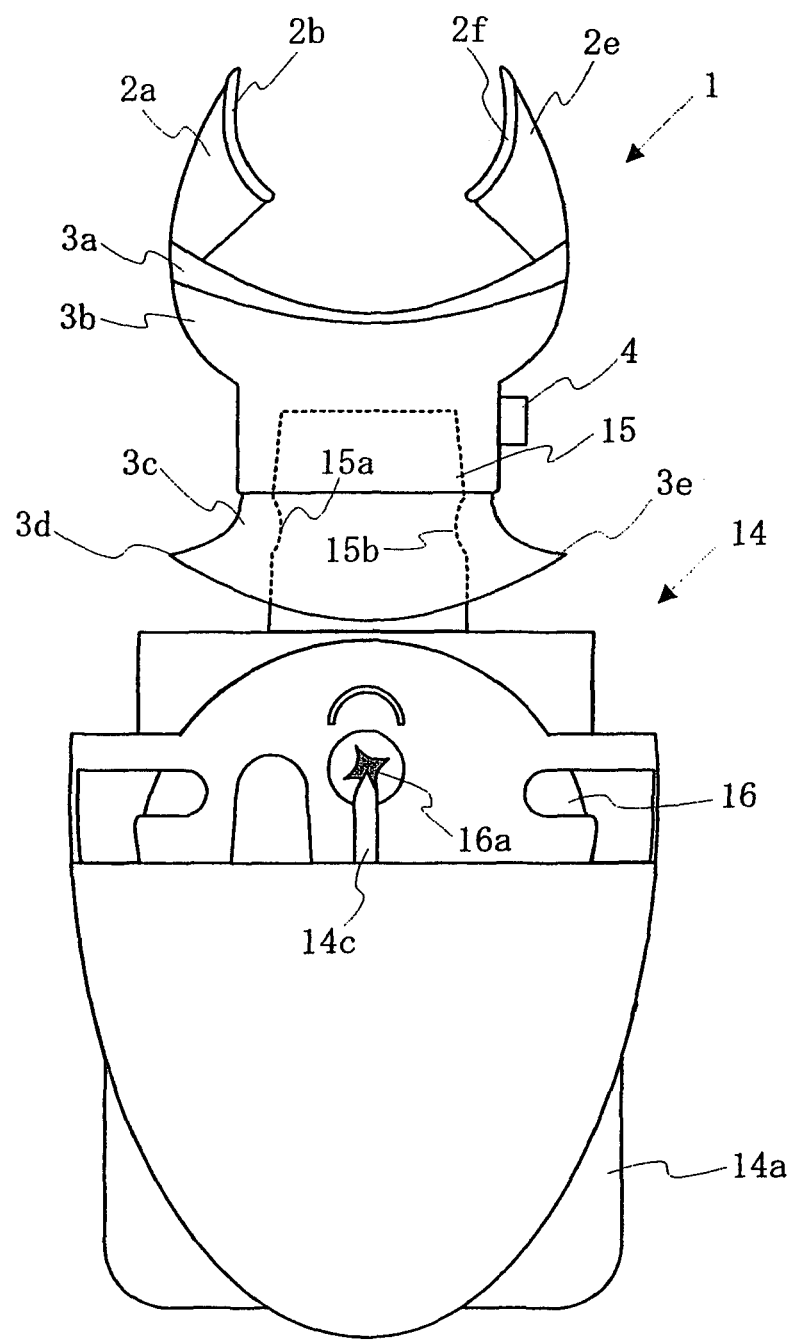
FIG. 14 is a front view when the inhaler aid with the reed for the minute powdery curative medicine of the present invention is used with a DISKHALER (registered trademark)
Figure 15:
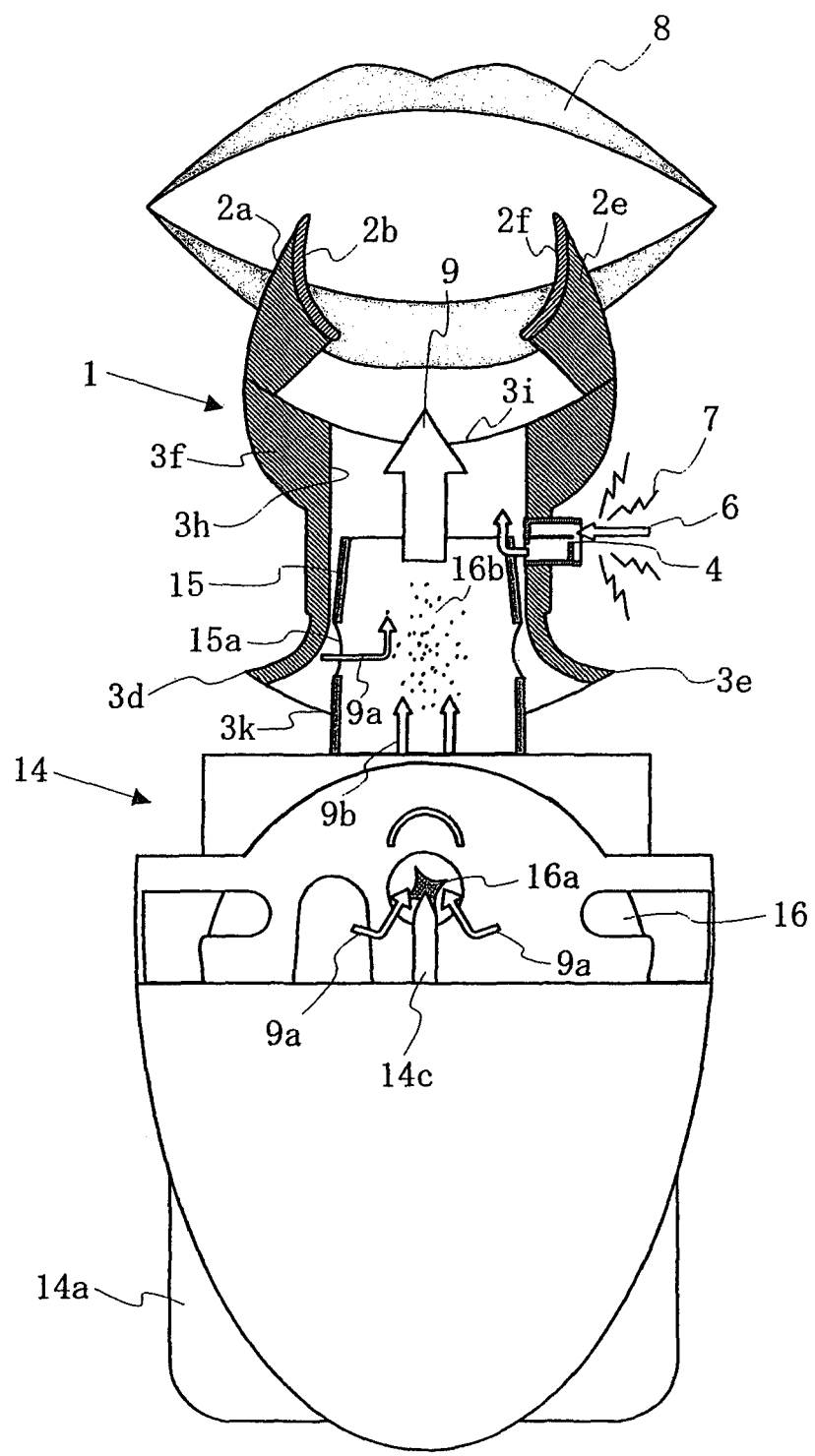
FIG. 15 is a partial sectional view when the inhaler aid with the reed for the minute powdery curative medicine of the present invention is used with the DISKHALER (registered trademark).

FIG. 14 and FIG. 15 are views showing the inhaler aid with the reed for the minute powdery curative medicine of the present invention which is used by being attached to a DISKHALER (registered trademark) 14, a conventionally used inhaler for the minute powdery curative medicine manufactured by GlaxoSmithKline Corporation.

As shown in FIG. 14, the inhaler aid 1 with the reed for the minute powdery curative medicine of the present invention is attached to the DISKHALER (registered trademark) 14 in the following method. A mouthpiece 15 of the DISKHALER (registered trademark) 14 is inserted into the junction aperture 3k of the inhaler aid 1 with the reed for the minute powdery curative medicine.

As shown in FIG. 15, a diameter of the inner peripheral surface 3h inside the tube 3b of the inhaler aid 1 with the reed for the minute powdery curative medicine of the present invention corresponds to a diameter of upper ends of left and right small holes 15a and 15b that are provided on left and right sides of the mouthpiece 15, so that a lower end of the inner peripheral surface 3h closely contacts and is fixed to the upper ends of the left and right small holes 15a and 15b of the mouthpiece 15. Therefore, the inhaler aid 1 with the reed for the minute powdery curative medicine can aid in the inhalation operation without completely covering the entire mouthpiece 15 and without interfering with the mechanism inherent to the DISKHALER (registered trademark) 14.

In other words, because the lower end of the inner peripheral surface 3h inside the tube 3b closely contacts the upper ends of the left and right small holes 15a and 15b of the mouthpiece 15, peripheries of the left and right small holes 15a and 15b are covered with the junction inner peripheral portion 3j of the inhaler aid 1 with the reed for the minute powdery curative medicine. However, an inner periphery of the junction inner peripheral portion 3j becomes larger in a horn shape toward the junction aperture 3k, so that the left and right small holes 15a and 15b can take in the air without being blocked, and functions are not damaged in the left and right small holes 15a and 15b which are provided to correct a difference between a lung breathing capacity and an air flow volume in the minute powdery medicine inhalation path to prevent breathing difficulty.

The DISKHALER (registered trademark) 14 to which the inhaler aid 1 with the reed for the minute powdery curative medicine is attached is used in the following method. First, the engagement portion 2 of the inhaler aid 1 with the reed for the minute powdery curative medicine attached to the mouthpiece 15 is held in the mouth 8, and the left and right projections 2a and 2e are bitten and fixed with teeth, and then the air 9 is breathed in.

When the air 9 is sucked in, the air 9a is taken into a ROTADISK 16 from a surface hole 16a pierced by a needle 14c on a surface of the ROTADISK 16 that is attached to a main unit 14a of the DISKHALER (registered trademark) 14. Also, the air 9a is taken in from the left and right small holes 15a and 15b formed in the mouthpiece 15.

The air 9a taken into the ROTADISK 16 from the surface hole 16a of the ROTADISK 16 whirls up a curative medicine 16b in the ROTADISK 16, and is released from the main unit 14a into the mouthpiece 15, and then the curative medicine 16b is inhaled, together with the air 9a taken into the mouthpiece 15 from the left and right small holes 15a and 15b, into the oral cavity through the inhalation path 5 of the inhaler aid 1 with the reed for the minute powdery curative medicine.

At this moment, the air 6 also is sucked from the reed 4 inserted into the tube 3b of the inhaler aid 1 with the reed for the minute powdery curative medicine, and vibrates the valve 4d, and then the air 6b is released into the inhalation path 5 through the flow chamber 4g, whereby the reed 4 produces the beep 7. Therefore, the beep 7 is produced only when the patient has correctly performed the inhalation operation, and the patient himself can ascertain that the inhalation operation has been correctly performed.

Industrial Applicability

The inhaler aid with the reed for the minute powdery curative medicine of the present invention has the following effects.

Firstly, the inhaler aid with the reed for the minute powdery curative medicine of the present invention can be used by being attached to the conventionally used inhalers for the minute powdery curative medicine with various configurations and shapes, and the sound is made from the reed, thereby allowing the patient himself, who inhales the curative medicine, to ascertain that the curative medicine has sufficiently been inhaled.

Secondly, the inhaler aid with the reed for the minute powdery curative medicine of the present invention is not only held in the mouth, but also bitten and fixed with teeth for inhalation, so that patients including elderly people and children who can not perform the inhalation operation can also sufficiently inhale the curative medicine by use of the present invention.

Thirdly, as the inhaler aid with the reed for the minute powdery curative medicine of the present invention is made of silicon rubber, it can be washed as needed to keep clean, and once one masters the use of the inhaler aid for the minute powdery curative medicine, the engagement portion can be cut away, allowing the inhaler aid to be used for a long time.

The invention claimed is:

1. An inhaler aid to be fitted to a mouthpiece of an inhaler for inhaling minute powdery curative medicine, said inhaler aid, comprising:
a main unit having a silicon rubber tube used to aid the inhaler for minute powdery curative medicine, and a horn-shaped junction at a lower portion of the main unit,
an engagement portion which is provided at an upper portion of the main unit, the engagement portion including left and right projections, each having a holding member at an end thereof; and
a reed fitted into a side of the main unit;
wherein when the inhaler aid is joined to a mouthpiece of the inhaler for the minute powdery curative medicine, a sound is produced from the reed only when an inhalation has been correctly performed,
wherein the horn-shaped junction includes a front joint piece and a rear joint piece, the front joint piece and the rear joint piece projecting further away from the engagement portion than left and right lateral ends of the horn-shaped junction,
wherein, when viewed from a direction where the left and right projections of the engagement portion overlap, the horn-shaped junction has an arched shape such that the front joint piece and the rear joint piece of the horn-shaped junction correspond to bases of the arched shape and the left and right lateral ends of the horn-shaped junction correspond to a top of the arched shape,
wherein an inhalation flow path in said main unit is defined by a junction inner peripheral portion and an inner peripheral surface, the junction inner peripheral portion corresponding to inner surfaces of said front joint piece, said rear joint piece, said left lateral end and said right lateral end,
wherein said junction inner peripheral portion tapers in a left-right direction and in a front-rear direction towards said inner peripheral surface,
wherein said inhaler is selected from the group consisting of:
(a) a disk-shaped inhaler having a mouthpiece shaped to fit the curved shape of the junction inner peripheral portion,
(b) an inhaler having longitudinally elongated air grooves and a mouthpiece with a cylindrical tapered portion, a lower portion of said inner peripheral surface being fittable with a lower portion of said mouthpiece, and
(c) an inhaler having a mouthpiece with holes formed on the left and right sides thereof, a diameter of said inner peripheral surface corresponding to a diameter of upper ends of said holes formed of the left and right sides of the mouthpiece,
wherein said inhaler aid is fittable to any one of inhalers (a), (b) or (c) while permitting inhalation of said minute powdery curative medicine and producing sound from said reed only when an inhalation has been correctly performed, and
wherein said inhaler aid is fittable to inhaler (a) such that an entirety of a surface of said junction inner peripheral portion contacts an entirety of a surface of said mouthpiece of said disk-shaped inhaler.

2. An inhaler aid to be attached to at least one type of inhaler, comprising:
a main unit having a tube used to release a minute powdery curative medicine therethrough, and a horn-shaped junction attachable to a mouthpiece of the inhaler,
an engagement portion which is provided at an upper portion of the main unit, the engagement portion including left and right projections, each having a holding member at an end thereof; and
a reed fitted into a side of the main unit;
wherein when the inhaler aid is joined to the mouthpiece of the inhaler for the minute powdery curative medicine, a sound is produced from the reed only when an inhalation has been correctly performed by whirling up the minute powdery curative medicine, wherein the horn-shaped junction includes a front joint piece and a rear joint piece, the front joint piece and the rear joint piece projecting further away from the engagement portion than left and right lateral ends of the horn-shaped junction, wherein, when viewed from a direction where the left and right projections of the engagement portion overlap, the horn-shaped junction has an arched shape such that the front joint piece and the rear joint piece of the horn-shaped junction correspond to bases of the arched shape and the left and right lateral ends of the horn-shaped junction correspond to a top of the arched shape, wherein an inhalation flow path in said main unit is defined by a junction inner peripheral portion and an inner peripheral surface, the junction inner peripheral portion corresponding to inner surfaces of said front joint piece, said rear joint piece, said left lateral end and said right lateral end, wherein said junction inner peripheral portion tapers in a left-right direction and in a front-rear direction towards said inner peripheral surface, wherein said inhaler is selected from the group consisting of:

(a) a disk-shaped inhaler having a mouthpiece shaped to fit the curved shape of the junction inner peripheral portion, (b) an inhaler having longitudinally elongated air grooves and a mouthpiece with a cylindrical tapered portion, a lower portion of said inner peripheral surface being fittable with a lower portion of said mouthpiece, and (c) an inhaler having a mouthpiece with holes formed on the left and right sides thereof, a diameter of said inner peripheral surface corresponding to a diameter of upper ends of said holes formed of the left and right sides of the mouthpiece, wherein said inhaler aid is fittable to any one of inhalers (a), (b) or (c) while permitting inhalation of said minute powdery curative medicine and producing sound from said reed only when an inhalation has been correctly performed, and wherein said inhaler aid is fittable to inhaler (a) such that an entirety of a surface of said junction inner peripheral portion contacts an entirety of a surface of said mouthpiece of said disk-shaped inhaler.

3. The inhaler aid according to claim 2, wherein said tube is formed of a silicon rubber.

* * * * *